(12) United States Patent
McNally et al.

(10) Patent No.: US 8,858,544 B2
(45) Date of Patent: Oct. 14, 2014

(54) SURGICAL INSTRUMENT GUIDE

(75) Inventors: David J. McNally, Salt Lake City, UT (US); Kim H. Manwaring, Phoenix, AZ (US); Mark Stringham, Salt Lake City, UT (US); Mark Shafer, West Valley City, UT (US)

(73) Assignee: Domain Surgical, Inc., Salt Lake City, UT (US)

( * ) Notice: Subject to any disclaimer, the term of this patent is extended or adjusted under 35 U.S.C. 154(b) by 376 days.

(21) Appl. No.: 13/471,972

(22) Filed: May 15, 2012

(65) Prior Publication Data

US 2013/0006240 A1     Jan. 3, 2013

Related U.S. Application Data

(60) Provisional application No. 61/486,623, filed on May 16, 2011.

(51) Int. Cl.
| | |
|---|---|
| *A61B 18/04* | (2006.01) |
| *A61B 17/3209* | (2006.01) |
| *A61B 17/32* | (2006.01) |
| *A61B 19/00* | (2006.01) |
| *A61B 18/14* | (2006.01) |

(52) U.S. Cl.
CPC . *A61B 17/3209* (2013.01); *A61B 2017/320052* (2013.01); *A61B 2019/4027* (2013.01); *A61B 2019/481* (2013.01); *A61B 18/1402* (2013.01); *A61B 2018/1412* (2013.01)
USPC ............................................................. 606/27

(58) Field of Classification Search
CPC ............... A61B 17/32; A61B 17/3209; A61B 2019/40; A61B 2019/4027; A61B 2019/48; A61B 2019/405; A61B 2017/320052; A61B 18/08; A61B 18/082; A61B 18/14; A61B 18/1402; A61B 2017/3211; A61B 2018/00601; A61B 2018/08
USPC ............................................................. 606/27
See application file for complete search history.

(56) References Cited

U.S. PATENT DOCUMENTS

| | | |
|---|---|---|
| 300,155 A | 6/1884 | Starr |
| 770,368 A | 9/1904 | Heath |

(Continued)

FOREIGN PATENT DOCUMENTS

| | | |
|---|---|---|
| EP | 0033958 | 8/1981 |
| EP | 0 130 671 | 9/1985 |

(Continued)

OTHER PUBLICATIONS

Translation of Office Action from related Japanese Patent Application No. 2012-506188, PCT US2010-031114.

(Continued)

*Primary Examiner* — Robert N Wieland
(74) *Attorney, Agent, or Firm* — Bateman IP

(57) ABSTRACT

A surgical instrument guide for facilitating treatment of a target tissue is provided. The surgical instrument guide may be placed between two groups of tissue such that a first group of tissue is cut and a second group of tissue is protected from being cut. The surgical instrument guide may lift tissue and slide tissue along a surface so that a target tissue may be cut to a desired depth more easily during a surgical procedure. The surgical instrument guide may be releasably attachable to a surgical instrument or integrally formed therewith.

21 Claims, 14 Drawing Sheets

(56) References Cited

U.S. PATENT DOCUMENTS

| | | | |
|---|---|---|---|
| 1,104,053 | A | 7/1914 | Lea |
| 1,280,052 | A | 9/1918 | Lidberg |
| 1,335,987 | A | 4/1920 | Reid |
| 1,366,231 | A | 1/1921 | Winter et al. |
| 1,401,104 | A | 12/1921 | Kruesheld |
| 1,794,296 | A | 2/1931 | Hyams |
| 2,027,854 | A | 1/1936 | Breth et al. |
| 2,050,904 | A | 8/1936 | Trice |
| 2,120,598 | A | 6/1938 | Beuoy |
| 2,250,602 | A | 7/1941 | Pierce |
| 2,278,633 | A | 4/1942 | Bagnall |
| 2,375,154 | A | 5/1945 | Volterra |
| 2,412,977 | A | 12/1946 | Eskin |
| 2,501,499 | A | 3/1950 | Crowley |
| 2,670,425 | A | 12/1954 | Stone |
| 2,735,797 | A | 2/1956 | Schjeldahl |
| 2,782,290 | A | 2/1957 | Lannan et al. |
| 2,831,242 | A | 4/1958 | Kieffer et al. |
| 2,846,560 | A | 8/1958 | Jacoby et al. |
| 2,863,036 | A | 12/1958 | Mitchell et al. |
| 2,947,345 | A | 8/1960 | Schjeldahl |
| 2,960,592 | A | 11/1960 | Pierce |
| 3,084,242 | A | 4/1963 | Vogler et al. |
| 3,213,259 | A | 10/1965 | Bennet et al. |
| 3,350,544 | A | 10/1967 | Lennox |
| 3,352,011 | A | 11/1967 | Alexander et al. |
| 3,400,252 | A | 9/1968 | Hayakawa |
| 3,404,202 | A | 10/1968 | Carlson et al. |
| 3,413,442 | A | 11/1968 | Buiting et al. |
| 3,414,705 | A | 12/1968 | Marcoux |
| 3,434,476 | A | 3/1969 | Shaw et al. |
| 3,501,619 | A | 3/1970 | Buiting et al. |
| 3,515,837 | A | 6/1970 | Ando |
| 3,520,043 | A | 7/1970 | Darling |
| 3,556,953 | A | 1/1971 | Schulz |
| 3,768,482 | A | 10/1973 | Shaw |
| 3,825,004 | A | 7/1974 | Durden, III |
| 3,826,263 | A | 7/1974 | Cage et al. |
| 3,834,392 | A | 9/1974 | Lampman et al. |
| 3,978,312 | A | 8/1976 | Barton et al. |
| RE29,088 | E | 12/1976 | Shaw |
| 4,089,336 | A | 5/1978 | Cage et al. |
| 4,091,813 | A | 5/1978 | Shaw et al. |
| RE30,190 | E | 1/1980 | Shaw |
| 4,185,632 | A | 1/1980 | Shaw |
| 4,196,734 | A | 4/1980 | Harris |
| 4,198,957 | A | 4/1980 | Cage et al. |
| 4,206,759 | A | 6/1980 | Shaw |
| 4,207,896 | A | 6/1980 | Shaw |
| 4,209,017 | A | 6/1980 | Shaw |
| 4,256,945 | A | 3/1981 | Carter et al. |
| 4,364,390 | A | 12/1982 | Shaw |
| 4,371,861 | A | 2/1983 | Abdelrahman et al. |
| 4,374,517 | A | 2/1983 | Hagiwara |
| RE31,723 | E | 11/1984 | Shaw |
| 4,481,057 | A | 11/1984 | Beard |
| 4,485,810 | A | 12/1984 | Beard |
| 4,492,231 | A | 1/1985 | Auth |
| 4,493,320 | A | 1/1985 | Treat |
| 4,523,084 | A | 6/1985 | Tamura et al. |
| 4,549,073 | A | 10/1985 | Tamura et al. |
| 4,600,018 | A | 7/1986 | James et al. |
| 4,622,966 | A | 11/1986 | Beard |
| 4,701,587 | A | 10/1987 | Carter et al. |
| 4,752,673 | A | 6/1988 | Krumme |
| 4,807,620 | A | 2/1989 | Strul |
| 4,839,501 | A | 6/1989 | Cowell |
| 4,848,337 | A | 7/1989 | Shaw et al. |
| 4,877,944 | A | 10/1989 | Cowell et al. |
| 4,914,267 | A | 4/1990 | Derbyshire |
| 4,915,100 | A | 4/1990 | Green |
| 4,938,761 | A | 7/1990 | Ensslin |
| 5,003,991 | A | 4/1991 | Takayama et al. |
| 5,047,025 | A | 9/1991 | Taylor et al. |
| 5,053,595 | A | 10/1991 | Derbyshire |
| 5,057,106 | A | 10/1991 | Kasevich et al. |
| 5,071,419 | A | 12/1991 | Rydell et al. |
| 5,087,256 | A | 2/1992 | Taylor et al. |
| 5,087,804 | A | 2/1992 | McGaffigan |
| 5,098,429 | A | 3/1992 | Sterzer |
| 5,107,095 | A | 4/1992 | Derbyshire |
| 5,182,427 | A | 1/1993 | McGaffigan |
| 5,189,271 | A | 2/1993 | Derbyshire |
| 5,197,649 | A | 3/1993 | Bessler et al. |
| 5,203,782 | A | 4/1993 | Gudov et al. |
| 5,211,646 | A | 5/1993 | Alperovich et al. |
| 5,217,460 | A | 6/1993 | Knoepfler |
| 5,300,068 | A | 4/1994 | Rosar et al. |
| 5,300,750 | A | 4/1994 | Carter, Jr. et al. |
| 5,308,311 | A | 5/1994 | Eggers et al. |
| 5,318,564 | A | 6/1994 | Eggers |
| 5,370,675 | A | 12/1994 | Edwards et al. |
| 5,376,094 | A | 12/1994 | Kline |
| 5,382,247 | A | 1/1995 | Cimino et al. |
| 5,400,267 | A | 3/1995 | Denen et al. |
| 5,411,508 | A | 5/1995 | Bessler et al. |
| 5,425,731 | A | 6/1995 | Daniel et al. |
| 5,445,635 | A | 8/1995 | Denen et al. |
| 5,472,443 | A | 12/1995 | Cordis et al. |
| 5,475,203 | A | 12/1995 | McGaffigan |
| 5,480,397 | A | 1/1996 | Eggers |
| 5,480,398 | A | 1/1996 | Eggers |
| 5,496,312 | A | 3/1996 | Klicek |
| 5,496,314 | A | 3/1996 | Eggers |
| 5,507,743 | A | 4/1996 | Edwards et al. |
| 5,540,679 | A | 7/1996 | Fram et al. |
| 5,540,681 | A | 7/1996 | Strul et al. |
| 5,542,916 | A | 8/1996 | Hirsch et al. |
| 5,571,153 | A | 11/1996 | Wallsten |
| 5,573,533 | A | 11/1996 | Strul |
| 5,593,406 | A | 1/1997 | Eggers et al. |
| 5,595,565 | A | 1/1997 | Treat et al. |
| 5,611,798 | A | 3/1997 | Eggers |
| 5,674,219 | A | 10/1997 | Monson et al. |
| 5,707,402 | A | 1/1998 | Heim |
| 5,807,392 | A | 9/1998 | Eggers |
| 5,836,874 | A | 11/1998 | Swanson et al. |
| 5,836,943 | A | 11/1998 | Miller, III |
| 5,911,719 | A | 6/1999 | Eggers |
| 5,964,759 | A | 10/1999 | Yamanashi et al. |
| 6,004,316 | A | 12/1999 | Laufer |
| 6,006,755 | A | 12/1999 | Edwards |
| 6,015,415 | A | 1/2000 | Avellanet |
| 6,035,238 | A | 3/2000 | Ingle et al. |
| 6,066,138 | A | 5/2000 | Sheffer et al. |
| 6,161,048 | A | 12/2000 | Sluijter et al. |
| 6,190,382 | B1 | 2/2001 | Ormsby et al. |
| 6,228,084 | B1 | 5/2001 | Kirwan, Jr. |
| 6,241,723 | B1 | 6/2001 | Heim et al. |
| 6,287,305 | B1 | 9/2001 | Heim et al. |
| 6,290,697 | B1 | 9/2001 | Tu et al. |
| 6,350,262 | B1 | 2/2002 | Ashley |
| 6,358,273 | B1 | 3/2002 | Strul et al. |
| 6,533,781 | B2 | 3/2003 | Heim et al. |
| 6,602,252 | B2 | 8/2003 | Mollenauer |
| 6,604,003 | B2 | 8/2003 | Fredricks et al. |
| 6,626,901 | B1 | 9/2003 | Treat et al. |
| 6,632,182 | B1 | 10/2003 | Treat |
| 6,692,489 | B1 | 2/2004 | Heim et al. |
| 6,726,683 | B1 | 4/2004 | Shaw |
| 6,821,273 | B2 | 11/2004 | Mollenauer |
| 6,860,880 | B2 | 3/2005 | Treat et al. |
| 6,908,463 | B2 | 6/2005 | Treat et al. |
| 6,911,026 | B1 | 6/2005 | Hall et al. |
| 6,912,911 | B2 | 7/2005 | Oh et al. |
| 6,980,862 | B2 | 12/2005 | Fredricks et al. |
| 6,980,865 | B1 | 12/2005 | Wang et al. |
| 7,011,656 | B2 | 3/2006 | McGaffigan |
| 7,083,613 | B2 | 8/2006 | Treat |
| 7,122,030 | B2 | 10/2006 | Flores et al. |
| 7,164,968 | B2 | 1/2007 | Treat et al. |
| 7,175,621 | B2 | 2/2007 | Heim et al. |
| 7,211,079 | B2 | 5/2007 | Treat |
| 7,211,080 | B2 | 5/2007 | Treat et al. |

(56) References Cited

U.S. PATENT DOCUMENTS

| | | |
|---|---|---|
| 7,235,073 B2 | 6/2007 | Levine et al. |
| 7,300,452 B2 | 11/2007 | Gleich |
| 7,317,275 B2 | 1/2008 | Treat |
| 7,326,202 B2 | 2/2008 | McGaffigan |
| 7,329,255 B2 | 2/2008 | McGaffigan |
| 7,377,919 B2 | 5/2008 | Heim et al. |
| 7,396,356 B2 | 7/2008 | Mollenauer |
| 7,473,250 B2 | 1/2009 | Makin et al. |
| 7,494,492 B2 | 2/2009 | Da Silva et al. |
| 7,528,663 B2 | 5/2009 | Naletov et al. |
| 7,533,719 B2 | 5/2009 | Hinson |
| 7,540,324 B2 | 6/2009 | de Rouffignac |
| 7,549,470 B2 | 6/2009 | Vinegar |
| 7,556,095 B2 | 7/2009 | Vinegar |
| 7,556,096 B2 | 7/2009 | Vinegar |
| 7,559,367 B2 | 7/2009 | Vinegar |
| 7,559,368 B2 | 7/2009 | Vinegar |
| 7,562,706 B2 | 7/2009 | Li et al. |
| 7,562,707 B2 | 7/2009 | Miller |
| 7,578,815 B2 | 8/2009 | Howell |
| 7,581,589 B2 | 9/2009 | Roes et al. |
| 7,584,789 B2 | 9/2009 | Mo et al. |
| 7,588,565 B2 | 9/2009 | Marchitto et al. |
| 7,588,566 B2 | 9/2009 | Treat et al. |
| 7,591,310 B2 | 9/2009 | Minderhoud |
| 7,597,147 B2 | 10/2009 | Vitek |
| 7,604,052 B2 | 10/2009 | Roes |
| 7,610,962 B2 | 11/2009 | Fowler |
| 7,613,523 B2 | 11/2009 | Eggers et al. |
| 7,631,689 B2 | 12/2009 | Vinegar |
| 7,631,690 B2 | 12/2009 | Vinegar |
| 7,632,295 B2 | 12/2009 | Flores |
| 7,635,023 B2 | 12/2009 | Goldberg |
| 7,635,024 B2 | 12/2009 | Karanikas |
| 7,635,025 B2 | 12/2009 | Vinegar |
| 7,702,397 B2 | 4/2010 | Fredricks et al. |
| 7,871,406 B2 | 1/2011 | Nields et al. |
| 7,922,713 B2 | 4/2011 | Geisel |
| 7,938,779 B2 | 5/2011 | Sakurai et al. |
| 7,951,149 B2 | 5/2011 | Carlton |
| 8,100,896 B2 | 1/2012 | Rodhajsky |
| 2001/0014804 A1 | 8/2001 | Goble et al. |
| 2002/0019644 A1 | 2/2002 | Hastings et al. |
| 2002/0120261 A1 | 8/2002 | Balbierz et al. |
| 2002/0173787 A1 | 11/2002 | Buysse et al. |
| 2003/0004507 A1 | 1/2003 | Francischelli et al. |
| 2003/0055417 A1 | 3/2003 | Truckai et al. |
| 2003/0055424 A1 | 3/2003 | Ciarrocca |
| 2003/0060818 A1 | 3/2003 | Kannenberg et al. |
| 2003/0073987 A1 | 4/2003 | Sakurai et al. |
| 2003/0073989 A1 | 4/2003 | Hoey et al. |
| 2003/0144660 A1 | 7/2003 | Mollenauer |
| 2003/0171747 A1 | 9/2003 | Kanehira et al. |
| 2003/0199755 A1 | 10/2003 | Halperin |
| 2004/0006335 A1 | 1/2004 | Garrison |
| 2004/0030330 A1 | 2/2004 | Brassell et al. |
| 2004/0034349 A1 | 2/2004 | Kirwan, Jr. et al. |
| 2004/0049185 A1 | 3/2004 | Latterell et al. |
| 2004/0059345 A1 | 3/2004 | Nakao et al. |
| 2004/0073256 A1 | 4/2004 | Marchitto |
| 2004/0167506 A1 | 8/2004 | Chen |
| 2004/0176756 A1 | 9/2004 | McGaffigan |
| 2004/0243120 A1 | 12/2004 | Orszulak et al. |
| 2005/0021016 A1 | 1/2005 | Malecki et al. |
| 2005/0033338 A1 | 2/2005 | Ferree |
| 2005/0072827 A1 | 4/2005 | Mollenauer |
| 2005/0107776 A1 | 5/2005 | Mcgaffigan et al. |
| 2005/0113824 A1 | 5/2005 | Sartor et al. |
| 2005/0197661 A1 | 9/2005 | Carrison et al. |
| 2005/0273111 A1 | 12/2005 | Ferree et al. |
| 2005/0283067 A1 | 12/2005 | Sobe |
| 2005/0283149 A1 | 12/2005 | Thorne et al. |
| 2005/0288659 A1 | 12/2005 | Kimura et al. |
| 2006/0127706 A1 | 6/2006 | Goebel et al. |
| 2006/0142824 A1 | 6/2006 | Zikorus et al. |
| 2006/0161149 A1 | 7/2006 | Privitera et al. |
| 2006/0167450 A1 | 7/2006 | Johnson et al. |
| 2006/0212030 A1 | 9/2006 | McGaffigan |
| 2006/0212031 A1 | 9/2006 | McGaffigan et al. |
| 2006/0217706 A1 | 9/2006 | Lau et al. |
| 2006/0241587 A1 | 10/2006 | Heim et al. |
| 2006/0241588 A1 | 10/2006 | Heim et al. |
| 2006/0241589 A1 | 10/2006 | Heim et al. |
| 2006/0271037 A1 | 11/2006 | Maroney et al. |
| 2007/0005054 A1 | 1/2007 | Heim et al. |
| 2007/0005055 A1 | 1/2007 | Heim et al. |
| 2007/0005056 A1 | 1/2007 | Heim et al. |
| 2007/0005057 A1 | 1/2007 | Heim et al. |
| 2007/0005058 A1 | 1/2007 | Heim et al. |
| 2007/0005059 A1 | 1/2007 | Heim et al. |
| 2007/0005060 A1 | 1/2007 | Heim et al. |
| 2007/0060920 A1 | 3/2007 | Weitzner |
| 2007/0073282 A1 | 3/2007 | McGaffigan et al. |
| 2007/0100336 A1 | 5/2007 | McFarlin et al. |
| 2007/0106294 A1 | 5/2007 | Nesbitt |
| 2007/0127897 A1 | 6/2007 | John et al. |
| 2007/0131428 A1 | 6/2007 | Boestert |
| 2007/0239151 A1 | 10/2007 | Atalar et al. |
| 2007/0270924 A1 | 11/2007 | McCann et al. |
| 2008/0017380 A1 | 1/2008 | Vinegar |
| 2008/0033419 A1 | 2/2008 | Nields et al. |
| 2008/0035346 A1 | 2/2008 | Nair et al. |
| 2008/0035347 A1 | 2/2008 | Brady |
| 2008/0035705 A1 | 2/2008 | Menotti |
| 2008/0038144 A1 | 2/2008 | Maziasz |
| 2008/0119841 A1 | 5/2008 | Geisel |
| 2008/0128134 A1 | 6/2008 | Mudunuri et al. |
| 2008/0135253 A1 | 6/2008 | Vinegar |
| 2008/0135254 A1 | 6/2008 | Vinegar |
| 2008/0142216 A1 | 6/2008 | Vinegar |
| 2008/0142217 A1 | 6/2008 | Pieterson |
| 2008/0161800 A1 | 7/2008 | Wang et al. |
| 2008/0173444 A1 | 7/2008 | Stone et al. |
| 2008/0174115 A1 | 7/2008 | Lambirth |
| 2008/0185147 A1 | 8/2008 | Vinegar |
| 2008/0217003 A1 | 9/2008 | Kuhlman |
| 2008/0217016 A1 | 9/2008 | Stegemeier |
| 2008/0236831 A1 | 10/2008 | Hsu |
| 2008/0249526 A1* | 10/2008 | Knowlton ............ 606/45 |
| 2008/0277113 A1 | 11/2008 | Stegemeier |
| 2008/0281310 A1 | 11/2008 | Dunning et al. |
| 2008/0281315 A1 | 11/2008 | Gines |
| 2008/0319438 A1 | 12/2008 | DeCarlo |
| 2009/0014180 A1 | 1/2009 | Stegemeier |
| 2009/0014181 A1 | 1/2009 | Vinegar |
| 2009/0093811 A1 | 4/2009 | Koblish et al. |
| 2009/0112200 A1 | 4/2009 | Eggers |
| 2009/0118729 A1 | 5/2009 | Auth et al. |
| 2009/0118730 A1 | 5/2009 | Mollenauer |
| 2009/0198224 A1 | 8/2009 | McGaffigan |
| 2009/0248002 A1 | 10/2009 | Takashino et al. |
| 2009/0292347 A1 | 11/2009 | Asmus et al. |
| 2009/0306644 A1 | 12/2009 | Mayse et al. |
| 2009/0312753 A1 | 12/2009 | Shadduck |
| 2010/0152725 A1 | 6/2010 | Pearson et al. |
| 2010/0198216 A1 | 8/2010 | Palanker |
| 2010/0268218 A1 | 10/2010 | Ormsby et al. |
| 2011/0004204 A1 | 1/2011 | Dodde et al. |

FOREIGN PATENT DOCUMENTS

| | | |
|---|---|---|
| EP | 2070486 | 6/2009 |
| GB | 2 022 974 | 12/1978 |
| GB | 1 546 624 | 5/1979 |
| JP | 03-051179 | 6/1987 |
| JP | 2558584 | 9/1996 |
| RU | 2 072 118 | 1/1997 |
| WO | WO-82/00746 | 3/1982 |
| WO | WO 92/17121 | 10/1992 |
| WO | WO-93/21839 | 11/1993 |
| WO | WO-96/26677 | 11/1996 |
| WO | WO 9937227 A1 | 7/1999 |
| WO | WO-01/06943 | 2/2001 |
| WO | WO-2004/014217 | 2/2004 |

(56) References Cited

FOREIGN PATENT DOCUMENTS

| WO | WO-2004/076146 | 9/2004 |
|---|---|---|
| WO | WO-2006/017517 | 2/2006 |
| WO | WO-2006/029649 | 3/2006 |
| WO | WO 2007080578 A2 | 7/2007 |
| WO | WO-2008/060668 | 5/2008 |

OTHER PUBLICATIONS

Written Opinion of the International Preliminary Examining Authority from related PCT Patent Application No. PCT/US2011/050417, Feb. 6, 2013.

Center for Research in Scientific Computation. *A Domain Wall Theory for Ferroelectric Hysteresis*, Jan. 1999.

International Preliminary Report on Patentability from related PCT Patent Application No. PCT/US2010/031114, Nov. 1, 2011.

International Search Report from related PCT Patent Application No. PCT/US2010/031114, Jan. 21, 2011.

Metcal Soldering Iron Catalog—2006.

URSI EMTS 2004, pp. 489-491, *Electromagnetic Probes for Living Tissue Cauterization*.

"High Temp Metals." NI2001201 Technical Data. High Temp Metals, Inc., n.d. Web. Jul. 13, 2012. <http://www.hightempmetals.com/techdatafnitempNi200data.php.

International Preliminary Report on Patentability from related PCT Patent Application No. PCT/US2012/032659, Nov. 23, 2012.

International Preliminary Report on Patentability from related PCT Patent Application No. PCT/US2012/038005, Nov. 23, 2012.

International Preliminary Report on Patentability from related PCT Patent Application No. PCT/US2012/032656, Oct. 23, 2012.

International Search Report and Written Opinion from related PCT Application US2012/038005, Nov. 19, 2013.

International Search Report and Written Opinion from related PCT Application US2012/032659, Oct. 8, 2013.

International Search Report and Written Opinion from related PCT Application US2012/032565, Oct. 8, 2013.

International Search Report and Written Opinion from related PCT Application US2012/032661, Aug. 19, 2013.

Visioli, Antonio. Practice PID Control: London: Springer-Verlag, 2006. 1-18. Print.

* cited by examiner

SURGICAL INSTRUMENT GUIDE

RELATED APPLICATIONS

The present application claims the benefit of U.S. Provisional Application Ser. No. 61/486,623, filed May 16, 2011, which is incorporated herein in its entirety.

THE FIELD OF THE INVENTION

The present invention relates to surgical instrument guides. More specifically, the present invention relates to guides for use with surgical instruments to facilitate cutting of certain tissue while protecting other tissues from being cut.

BACKGROUND

In surgery, a surgeon cuts into tissue at defined locations to access underlying structures or to perform some desirable restructuring of the tissue being cut. Damage to tissues outside of the defined location is usually undesirable. In some cases, a surgeon may wish to prevent damage to tissues underneath a tissue to be cut. Thus, a surgeon may need to carefully examine the depth of the cut while monitoring the length of cut and other variables—such as heat transfer to surrounding tissue, blood loss in the tissue, etc. This monitoring of multiple variables may cause the surgeon to take a slower approach to cutting through tissue or may cause a momentary distraction which results in tissue damage beyond that desired by the surgeon.

In some cases, a surgeon may use multiple tools to separate a tissue to be cut and other tissue(s) he or she wishes to avoid cutting. The use of multiple tools may demand the surgeon's otherwise free hand or require the surgeon to switch back and forth between instruments. In fact, in electrosurgical applications, a surgeon may use an instrument to separate or retract tissue with one hand, use the other hand to operate a cutting instrument and control the power output with a foot pedal to avoid having to let go of either the cutting instrument or the separating/retracting instrument. Thus, a surgeon may have to concentrate on simultaneously using at least three of his or her appendages during an operation.

Thus, there is a need for an improved device and method for reducing the number of variables that require the surgeon's attention such that the speed of surgery may be increased and/or the risk to the patient may be decreased. Additionally, it is desirable that the improved device and method reduce collateral tissue damage outside of a defined surgical location.

SUMMARY OF THE INVENTION

It is an object of the present invention to provide an improved to surgical instrument guide.

According to one aspect of the invention, a surgical instrument guide may be placed between two groups of tissue such that a first group of tissue is cut and a second group of tissue is protected from being cut.

According to another aspect of the invention, a surgical instrument guide may lift tissue and slide tissue along a surface such that the tissue stretches and a straight cut may be made more easily during a surgical procedure. As the cutting blade or surgical element may be recessed within the guide, the guide may lift and direct a cut such that cutting does not release an adjacent portion of tissue that may be cut.

According to another aspect of the invention, the surgical instrument guide may be attached to existing surgical instruments either permanently, or may be attached and removed whenever desired.

These and other aspects of the present invention are realized in a surgical instrument guide as shown and described in the following figures and related description.

BRIEF DESCRIPTION OF THE DRAWINGS

Various embodiments of the present invention are shown and described in reference to the numbered drawings wherein.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

Figure 1:
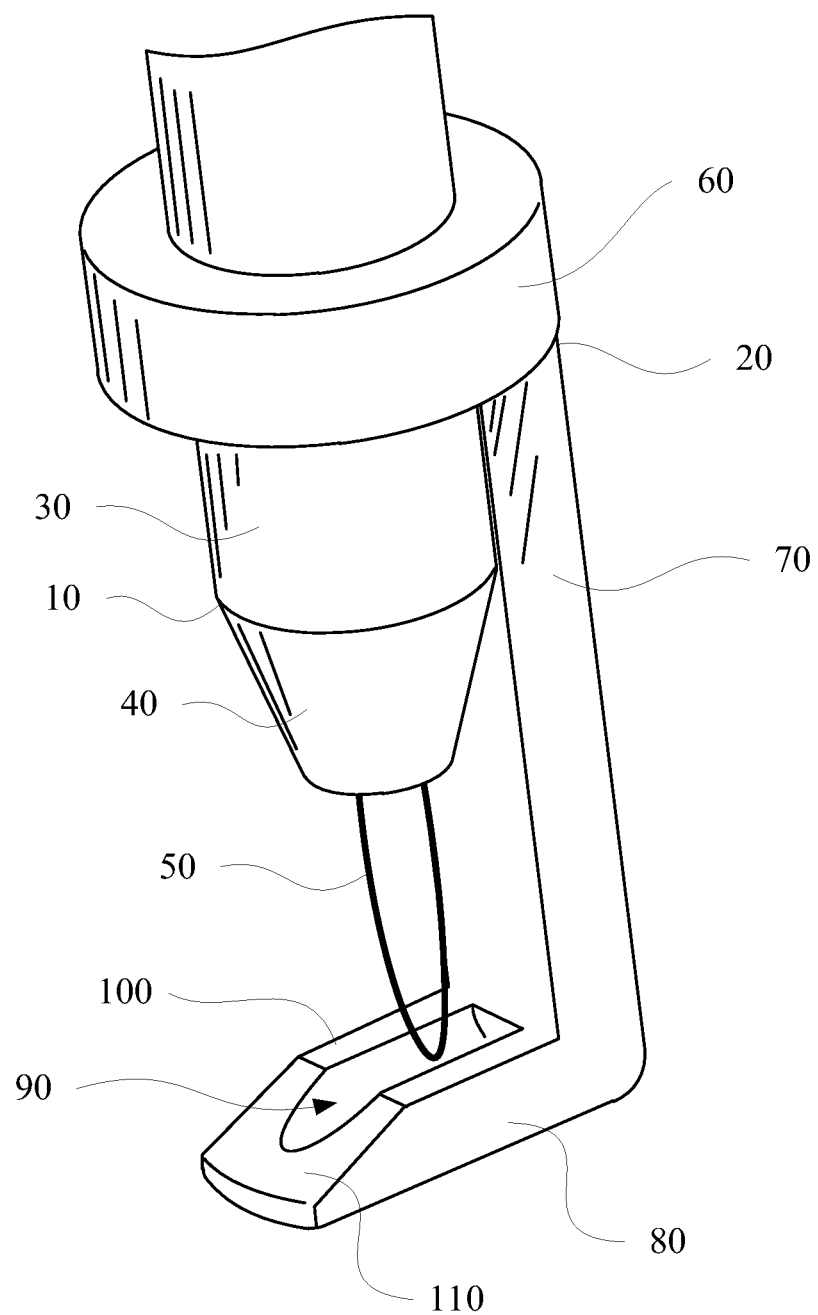
FIG. 1 shows a perspective view of the working end of a surgical tool with a surgical instrument guide attached thereto.

Turning now to FIG. 1, there is shown a perspective view of the working end of a surgical instrument 10 engaged with a surgical instrument guide 20 according to principles of the present invention. The working end of the surgical instrument 10 may engage the surgical instrument guide 20 to aid in surgery. The surgical instrument guide 20 may aid the surgeon in treating a target tissue while substantially preventing undesired damage in other tissue adjacent the target tissue. For example, the surgical instrument guide 20 may facilitate cutting of the target tissue while substantially preventing cutting of tissue adjacent the target tissue. It will be appreciated that the term "tissue" as used herein may refer to a single tissue type, a single tissue layer, multiple tissue types, multiple tissue layers, and/or other material on which a surgical instrument may be used.

In accordance with one aspect of the invention, a surgical instrument guide may cause a target tissue to be spaced apart from a tissue adjacent the target tissue prior to and/or during treatment of the target tissue by a surgical instrument. For example, the surgical instrument guide 20 may lift up and direct a target tissue toward an active element 50 of the surgical instrument 10. By lifting and directing the target tissue, a degree of separation and/or barrier may be made between the target tissue being cut and other tissue thus substantially preventing damage to the other tissue by the active element 50. The active element 50 may use thermal energy to treat tissue. For example, the active element 50 may include a ferromagnetic coated conductor to treat tissue such as thermally adjustable ferromagnetic conductors disclosed in U.S. Publication Nos. 2010-0268207, 2010-0268214, 2010-0268208, 2010-0268209, 2010-0268215, 2010-0268205, 2010-0268210, 2010-0268212, 2010-0268213, 2010-0268211, 2010-0268216, 2010-0268206, all of which are expressly incorporated herein by reference.

The guide 20 may engage the surgical instrument 10 such that a sufficient transfer of thermal energy from the active element 50 to the guide 20 in order to heat the guide is substantially prevented. Under these circumstances, the likelihood of thermal damage to any tissue contacted by the guide 20 is decreased or even eliminated. Thus, the guide 20 may aid a user to direct the active element 50 of the surgical tool to only specific tissue.

The working end of the surgical tool 10 may include a body 30, a tip 40 and an active element 50. The active element 50 may be a conventional cutting blade or an electrosurgical cutting element. The surgical instrument guide 20 may include a coupling member, such as a collar 60, an arm 70 which extends away from the surgical instrument 10 and a tissue shield 80 formed as a foot or other extension for protecting tissue other than the target tissue from being cut, etc. The surgical instrument guide 20 may be attached to the surgical instrument 10 by connecting the coupling member 60 to the body 30, for example, by slidably engaging the coupling member 60 with the body 30. The arm 70 may extend past the tip 40 such that tissue shield 80 is positioned a short distance beyond the active element 50. The tissue shield 80 has a top surface 100 and a bottom surface, and may include a channel, groove or depression 90 that allows the active element 50 to extend beyond the top surface 100 (but preferably not below the bottom surface) of the tissue shield 80 without contacting the tissue shield 80. Thus, the active element 50 may be said to intersect a plane extending along the top surface 100 of the tissue shield 80. According to one aspect of the invention, the guide 20 is connected to the surgical instrument 10 such that the active element 50 extends into the channel 90. Thus, the active element 50 may engage tissue that is positioned across the top surface 100 of the tissue shield 80 (e.g. the target tissue) and cut completely through the target tissue while the tissue shield 80 prevents the active element 50 from contacting tissue(s) along the bottom surface of the tissue shield 80.

A chamfer, incline or wedge, etc. 110 may be used to engage a target tissue and aid in lifting the target tissue away from other tissue(s) prior to treating the target tissue using the active element 50. As the wedge 110 slides along the tissue, it lifts the target tissue away from lower tissues and stretches it slightly over and across the top surface 100 of the tissue shield 80 and channel 90. This facilitates cutting the tissue cleanly. Tissue that is not pulled to the top of the tissue shield 80 may be pushed under the tissue shield 80. Thus, the tissue shield 80 may act as a barrier to prevent damage to any tissue under the tissue shield 80 caused by the active element 50.

It should be recognized that while the tools may be discussed in a surgical sense, such as surgical instrument 10, the system may have applicability in other areas, such as the cutting of meat or other membranes. For ease of understanding, however, the system may be described in a surgical context.

Figure 2:
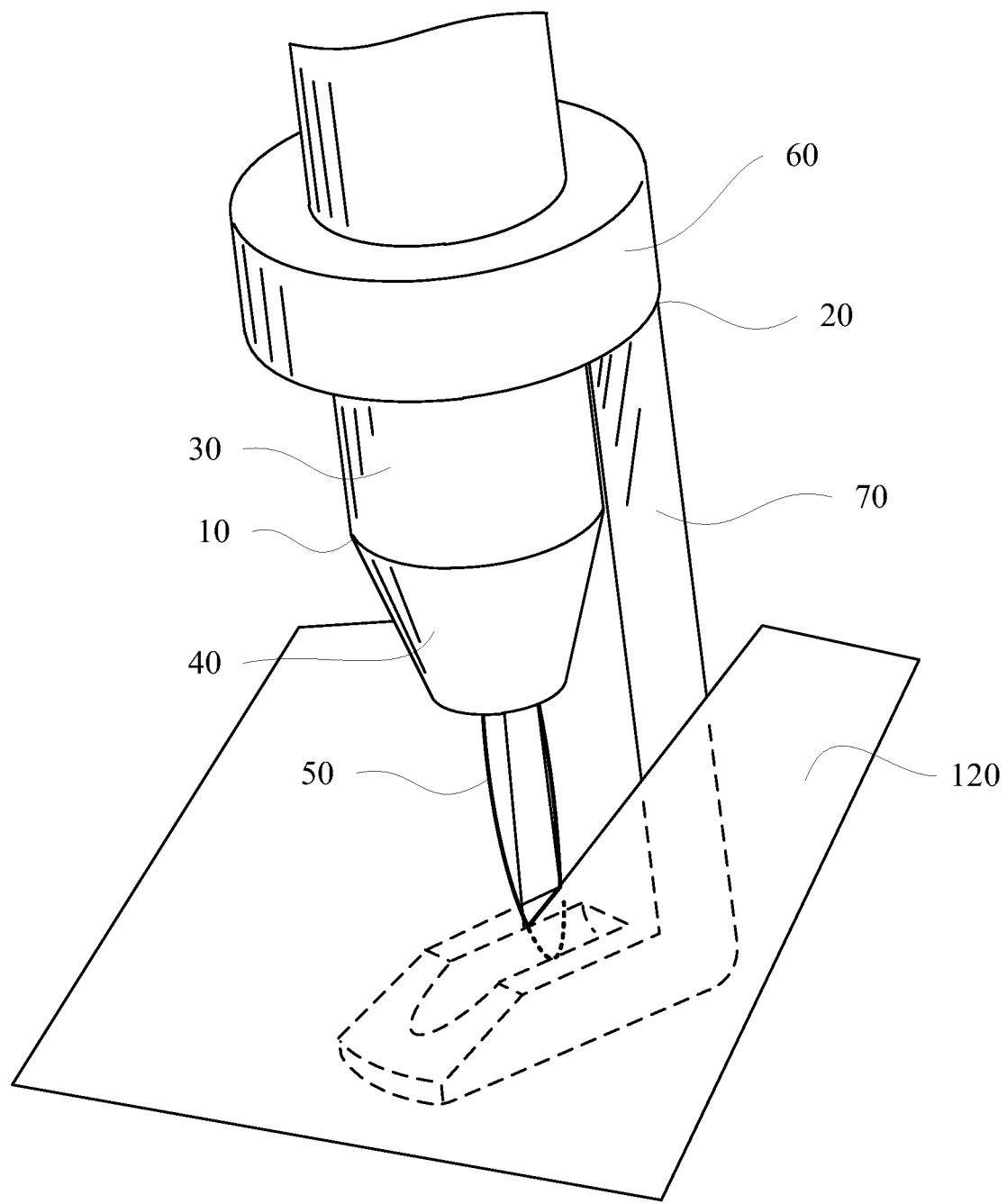
FIG. 2 shows a perspective view of the surgical tool of FIG. 1 cutting through tissue with the surgical instrument guide attached.

Turning now to FIG. 2, a perspective view of a surgical instrument 10 with guide 20 cutting through tissue 120 is shown. When the surgical instrument 10 is moved in a forward direction, the wedge 110 (FIG. 1) of the tissue shield 80 lifts the tissue 120 up and away from structures beneath the tissue 120 and slides along the tissue 120 as the active element 50 is advanced. As the active element 50 may cut the tissue 120, the cut portions of the tissue slide by the arm 70 which may be beveled or otherwise contoured depending on the application. Thus, the guide 20 may ensure that the cut along tissue 120 is made at a desired depth allowing the user to focus on the direction of the cut. Therefore, the tissue guide 20 may allow the user to perform a quicker cut with less risk of unintended damage.

Figure 2A:
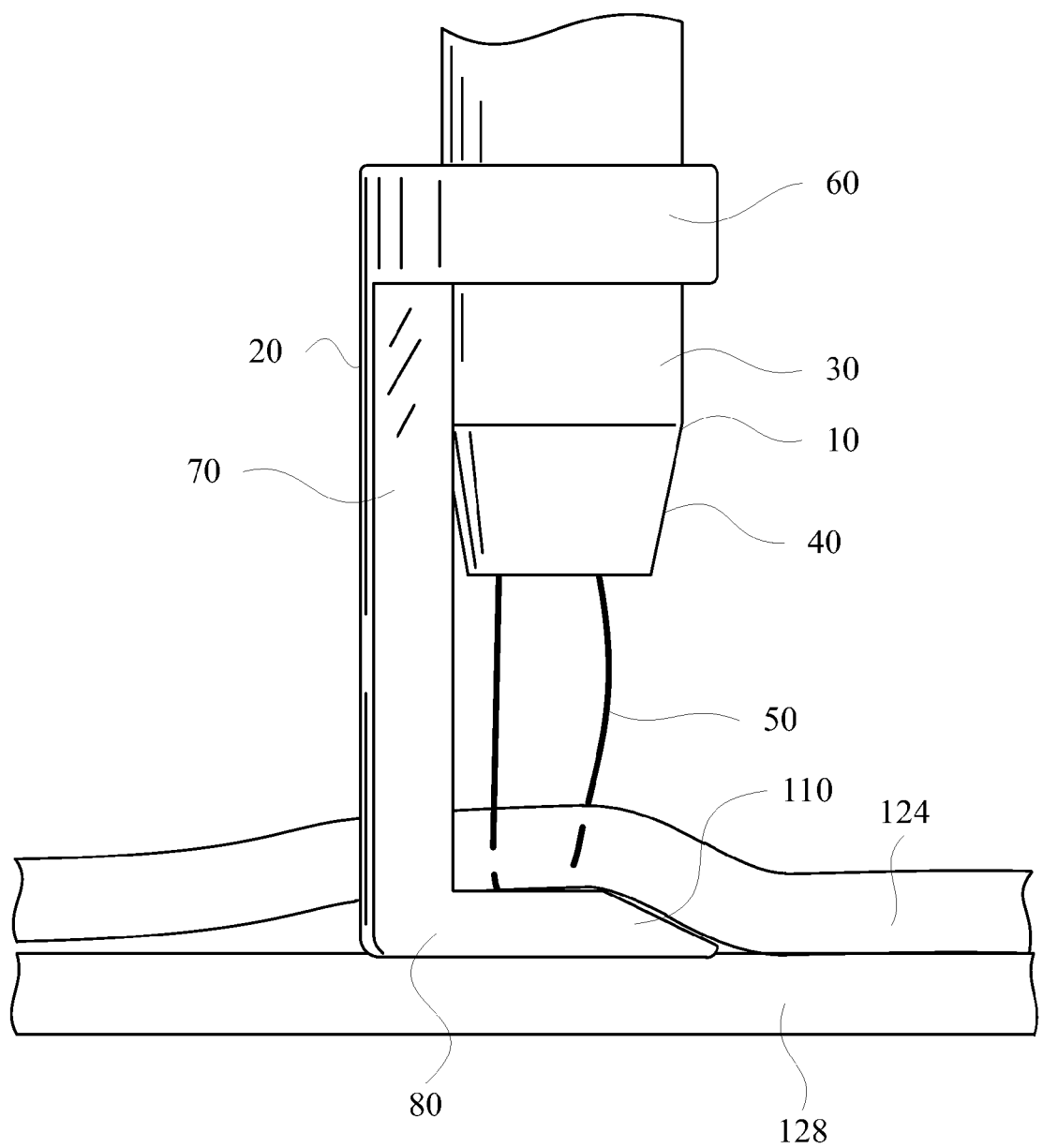
FIG. 2A shows a side view of the surgical tool of FIG. 1 and the surgical instrument guide cutting through a top layer of tissue while preventing the cutting of a lower layer of tissue.

Turning now to FIG. 2A, there is shown a side view of a the working end of a surgical instrument 10 as shown in FIGS. 1 and 2 as the guide 10 is moved through a first layer of tissue 124 above a second layer of tissue 128. Those skilled in the art will appreciate that there are numerous situations in which a surgeon desires to cut one layer of tissue and not another. For example, the spinal cord is wrapped in a membrane called the Dura Mater. A surgeon may need to access the spinal cord, but does not desire to cut into the spinal cord. To open the Dura Mater, the physician need only make a very small incision in the membrane and then slide the tissue shield 80 through the incision so that the tissue shield is disposed between the spinal cord and the Dura Mater. Once this is accomplished, the surgeon can cut along the Dura Mater without fear that he or she is also cutting into the spinal cord. There are numerous similar structures in the body where it is desirable for one layer of tissue to be cut without cutting an adjacent layer of tissue. The guide 20 both protects the underlying tissue 128 and lifts and helps separate the upper tissue 124 during cutting, thereby simplifying the procedure for the surgeon.

Figure 3:
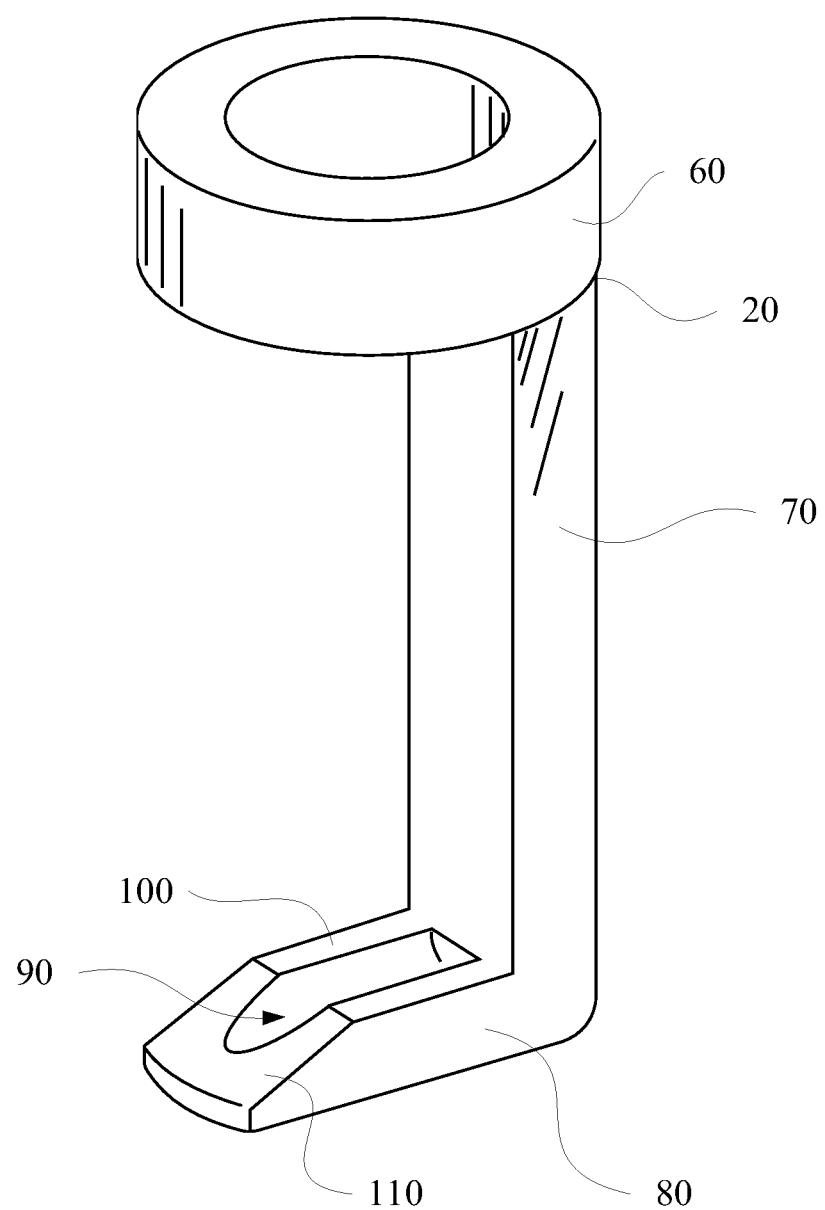
FIG. 3 shows a perspective view of a surgical instrument guide according to principles of the present invention.

Turning now to FIGS. 3 to 8 generally, different perspectives of a surgical tool guide 20 are shown. FIG. 3 shows a perspective view of the surgical guide 20. It will be appreciated that the guide 20 may be independent from the surgical instrument 10 with which the guide 20 is used. The guide 20 may be snap fit, have a threaded engagement or otherwise attach to the surgical instrument 10. Thus, in some embodiments, the guide 20 may be used only when desired and then removed so as to not interfere with the surgeon's use of the surgical instrument 10 during the remainder of the procedure.

As shown in FIG. 3, the lower portion of tissue shield 80 of the guide is disposed generally perpendicular to the arm 70. It will be appreciated that a variety of angles may be desirable for use in different medical procedures and the view in FIG. 3 should be deemed to be only exemplary of the principles of the present invention.

Figure 4:
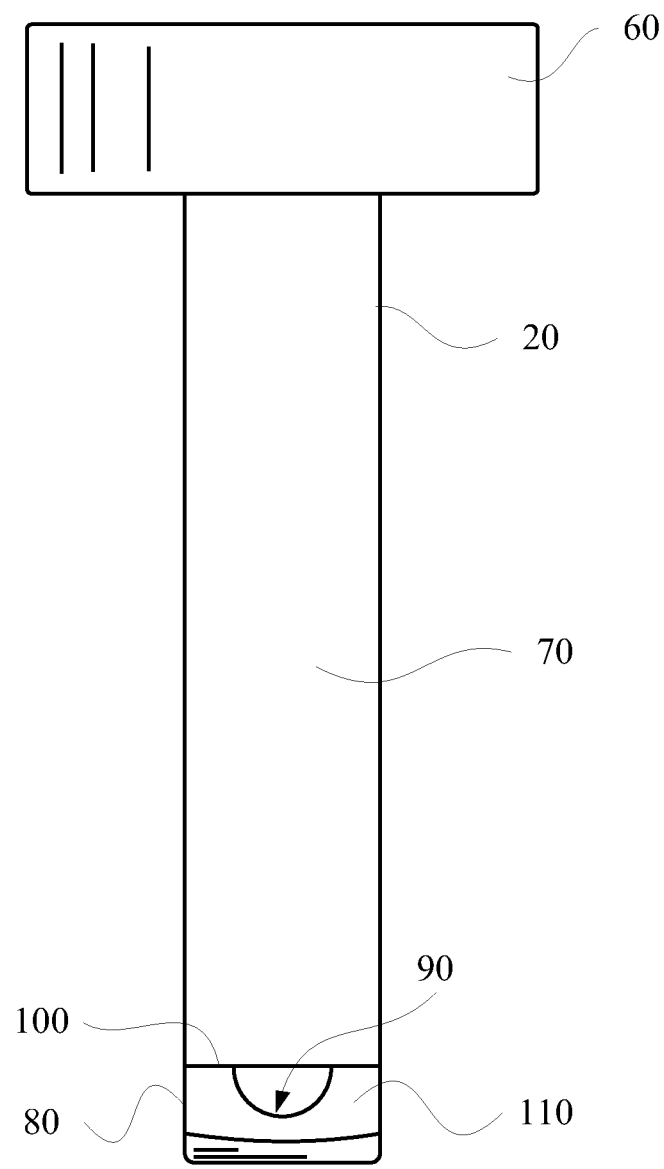
FIG. 4 shows a front view of a surgical instrument guide.

FIG. 4 shows a front view of a surgical tool guide shown in FIGS. 1-3. FIG. 4 provides a clearer view of the groove or channel 90 into which the cutting or active element (not shown) may extend so as to clearly cut through tissue passing up the incline or wedge 110 and over the top surface 100 of the tissue shield 80.

Figure 5:
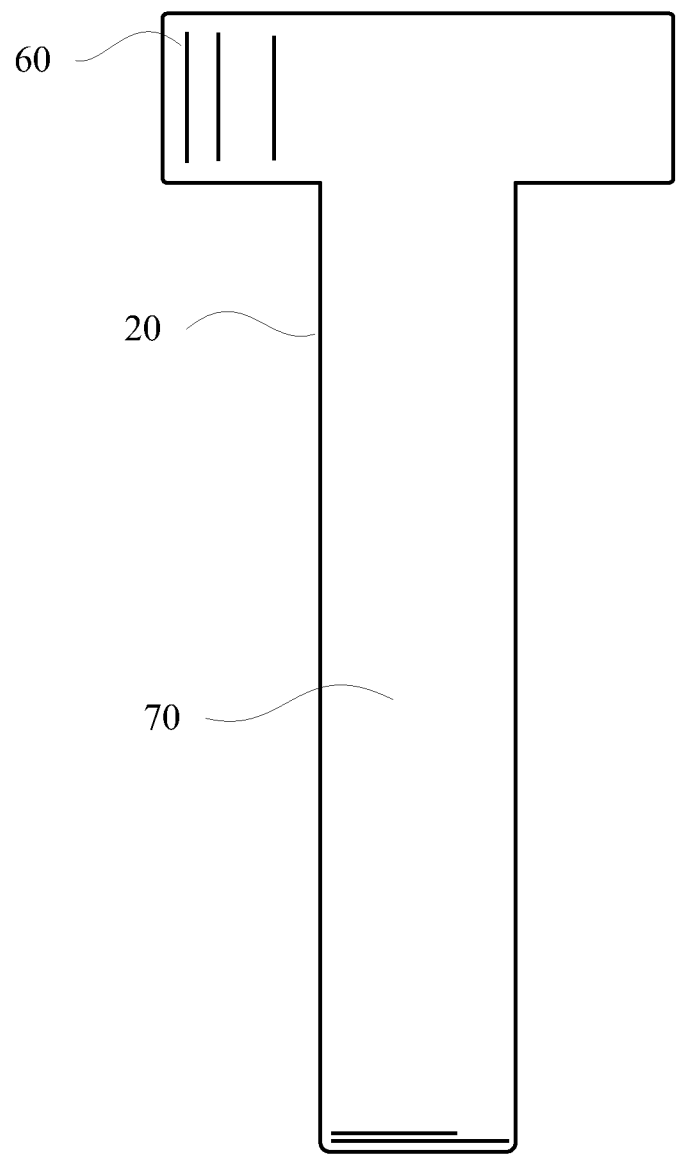
FIG. 5 shows a rear view of a surgical instrument guide.

FIG. 5 shows a rear view of a surgical instrument guide 20. While the arm 70 is shown as being fairly broad, it will be appreciated that the arm 70 can be thin and may be tapered or have a beveled edge to facilitate spreading apart of target tissue or tissues which are cut.

Figure 6:
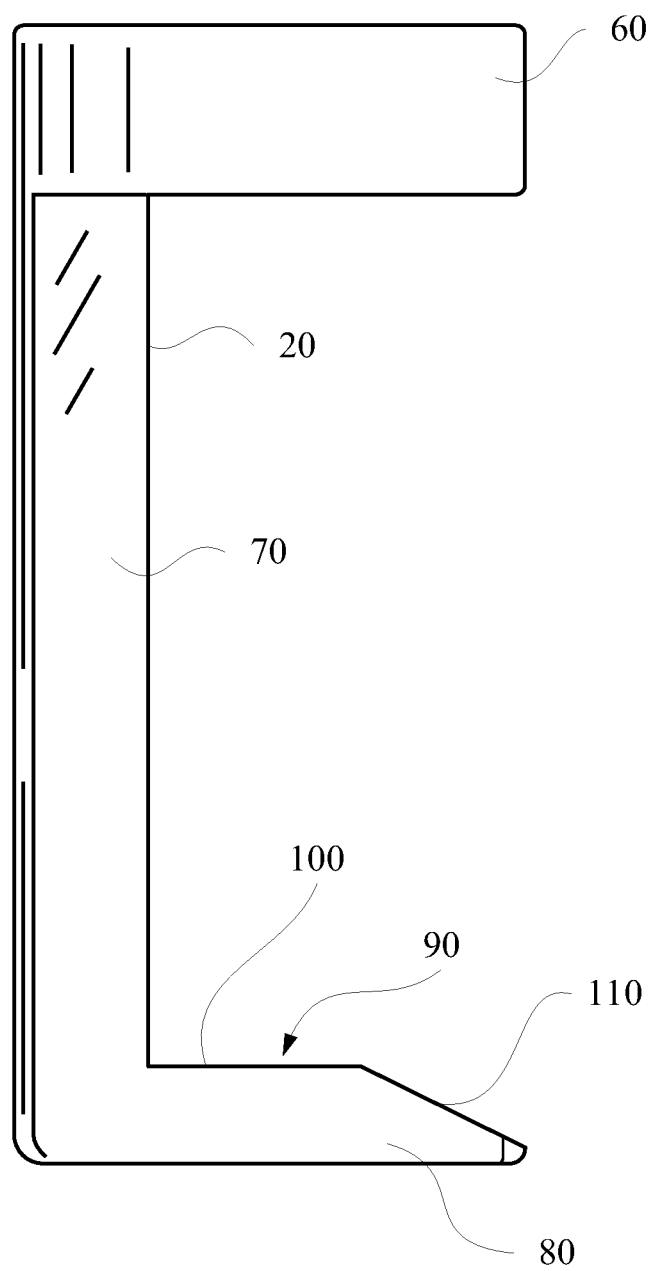
FIG. 6 shows a side view of a surgical instrument guide.

FIG. 6 shows a side view of the surgical instrument guide. FIG. 6 provides a better view of the incline or wedge 110 at the front of the tissue shield 80 that helps lift the target tissue over the channel 90 to facilitate cutting of the target tissue.

Figure 7:
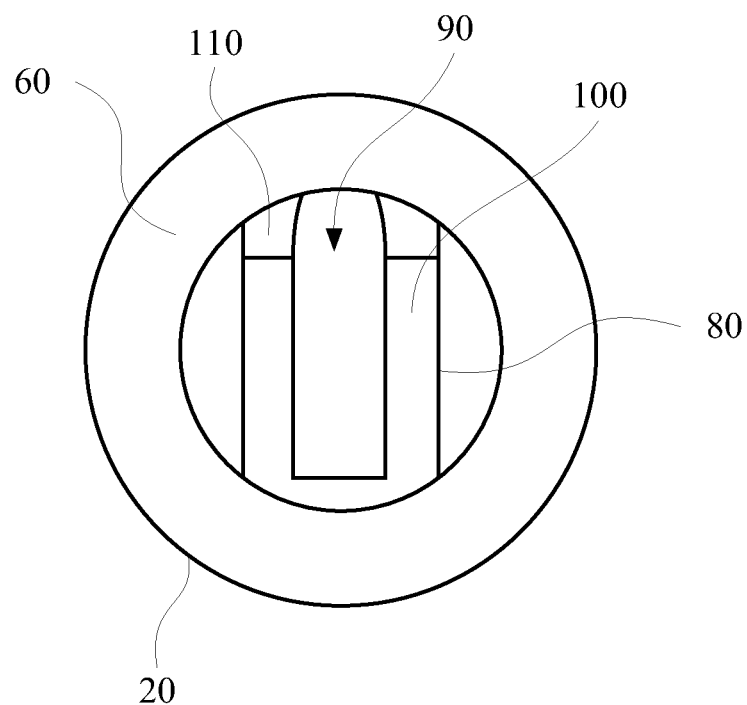
FIG. 7 shows a top view of a surgical instrument guide.
Figure 8:
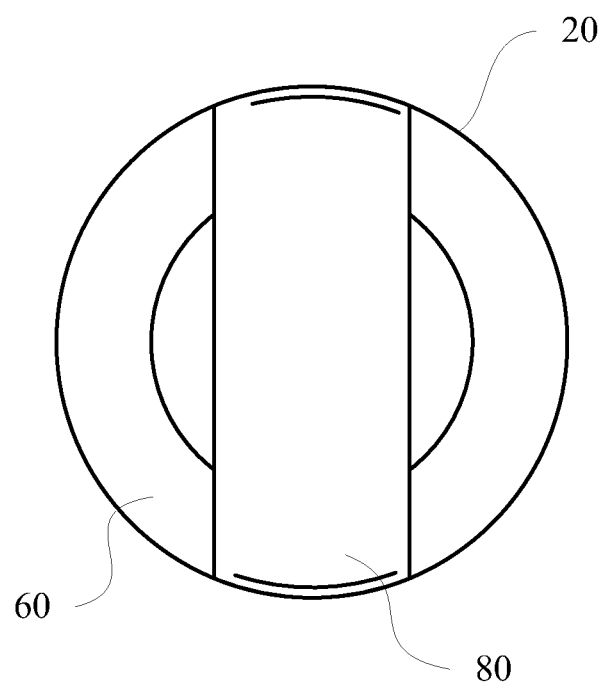
FIG. 8 shows a bottom view of a surgical instrument guide.

FIGS. 7 and 8 show a top view and bottom view, respectively, of the surgical instrument guide 20 shown in FIGS. 1-6. The top view looks through an opening in the coupling member 60 through which a portion of a surgical instrument may extend, such as the working end of a scalpel or electrosurgical element. The coupling member 60 may include a variety of attachment mechanisms for holding the guide 20 in place, such as depressions or projections which interact with the tool, a snap fit, etc. FIG. 7 also shows a top view of portions of the tissue shield 80, including the depression or channel 90 and the incline or wedge 110 which lifts the target tissue onto the top surface 100 of the tissue shield 80 for cutting.

FIGS. 1-8 show various parts of the surgical tool guide 20. For example, a surgical tool guide 20 according to principles of the present invention may include a coupling member 60 (such as a collar), an arm 70 and a tissue shield 80. The tissue shield 80 may contain a channel or depression 90, a top surface 100 and a wedge 110. It will be appreciated that the embodiment shown in FIGS. 1-8 is intended to be exemplary only, and is not intended to limit the scope of the principles of the present invention.

Figure 9:
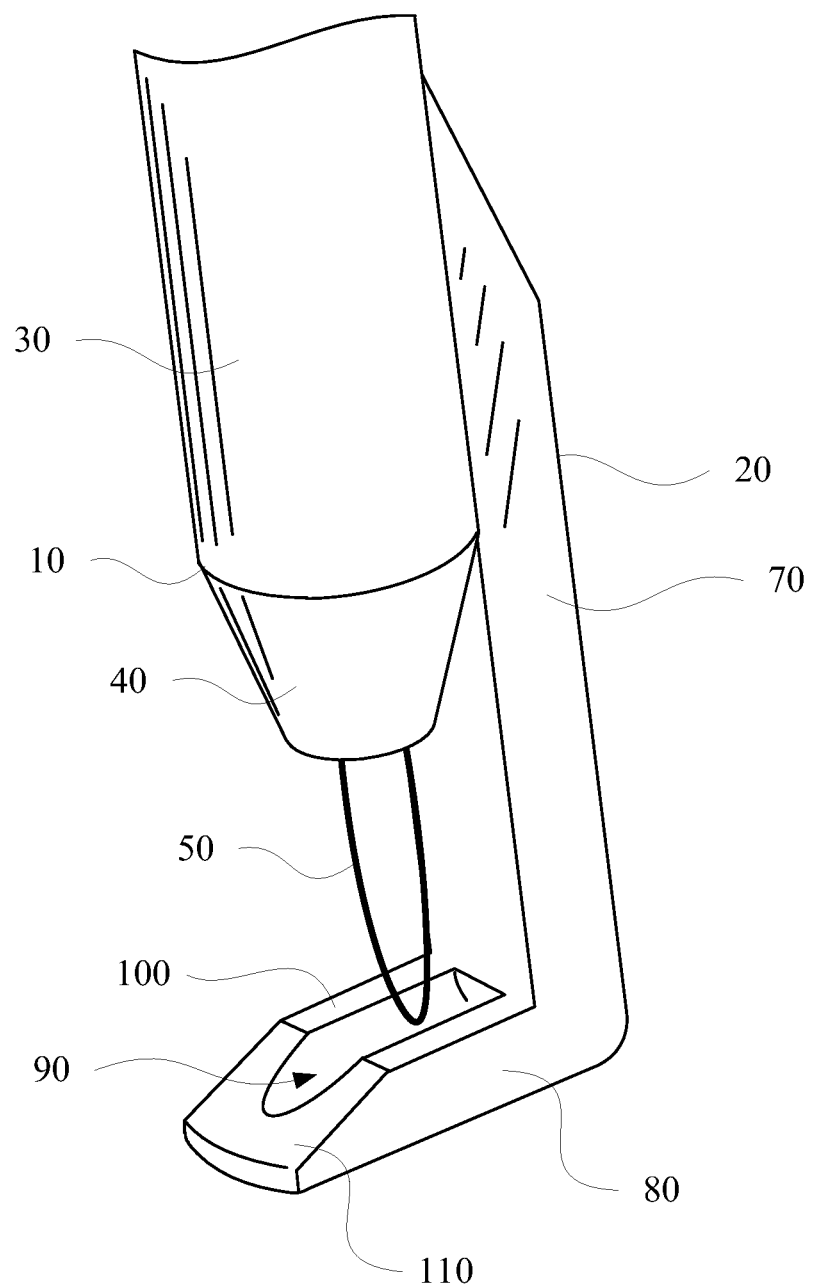
FIG. 9 shows a perspective view of a surgical instrument having an integral surgical instrument guide.
Figure 10:
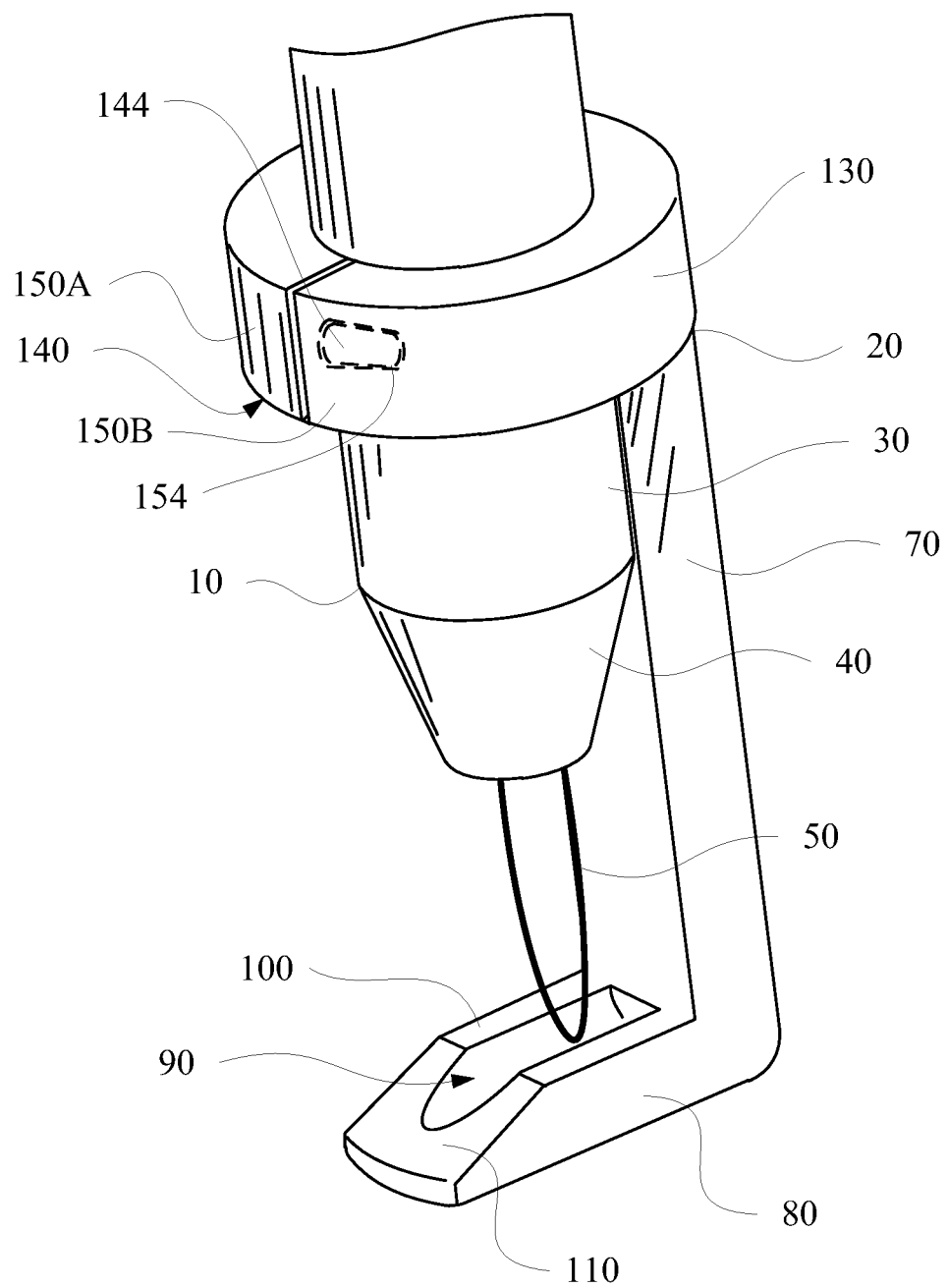
FIG. 10 shows a perspective view of a snap-on surgical instrument guide.

FIGS. 9 and 10, show different mechanisms of connecting the guide 20 to a surgical instrument 10. The guide 20 may be attached or coupled to the surgical tool 10 in multiple ways. In FIG. 9, the guide 20 is integrally formed with the surgical instrument body 30 and thus remains with the surgical instrument throughout use. The arm 70, integrally formed with the surgical tool body 30, extends down to the tissue shield 80. Thus, the entire device body, including the guide 20, may be formed as one piece.

In FIG. 10, the guide 20 includes a snap-on collar 130. According to one aspect of the invention, the snap-on collar 130 may be held on by elastic force. According to another aspect of the invention, a collar joint 140 includes a protrusion 144 from a first collar section 150A that slides into a channel 154 of a second collar section 150B. The engagement between the protrusion 144 and the channel 154 may lock and thus become essentially permanent, or may be releasable.

Figure 10A:
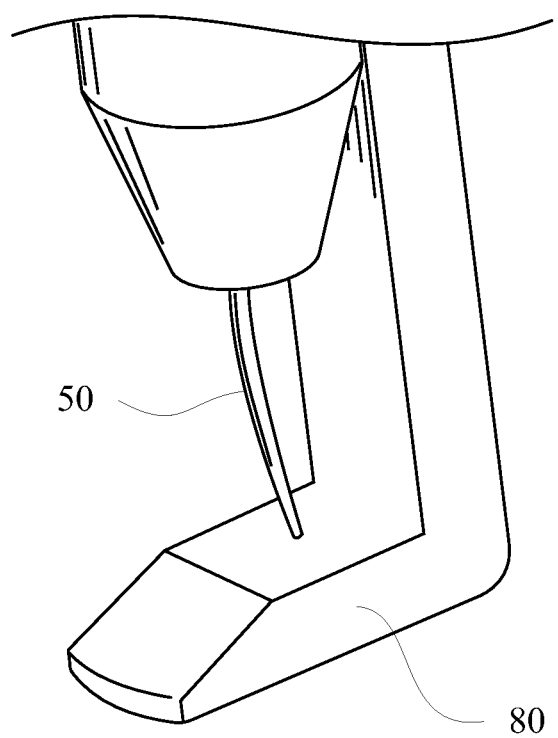
FIG. 10A shows a fragmented, perspective view of a surgical instrument and a surgical instrument guide according to principles of the present invention.

While the figures show a channel or depression 90, it should be recognized that other configurations are possible. For example, the tissue shield 80 may be constructed without a channel 90 and the active element 50 may extend so as to be substantially adjacent the top surface 100 of the top surface 100 of the tissue shield 80. According to another aspect of the invention, the active element 50 may extend into the tissue shield 80 as shown in FIG. 10A.

Figure 11:
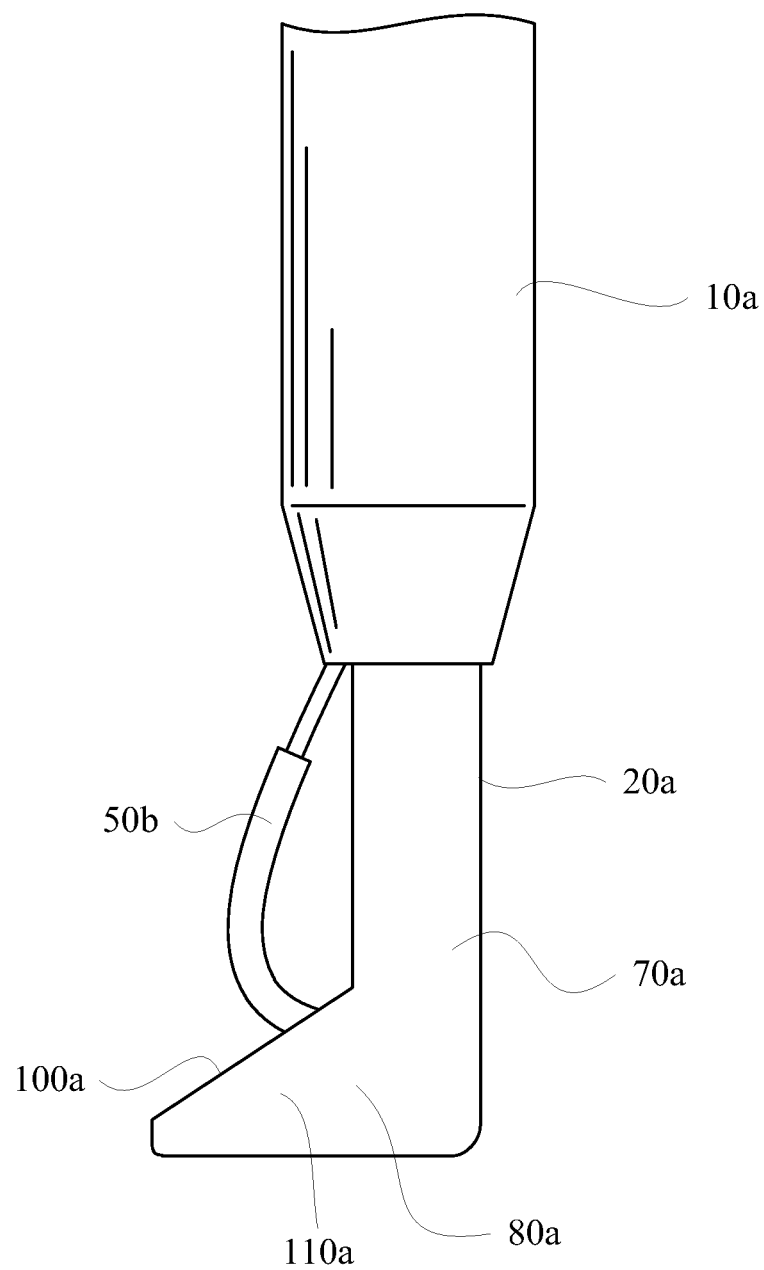
FIG. 11 shows a side view of an upward ramp surgical instrument guide generally positioned perpendicular to the surgical instrument.
Figure 12:
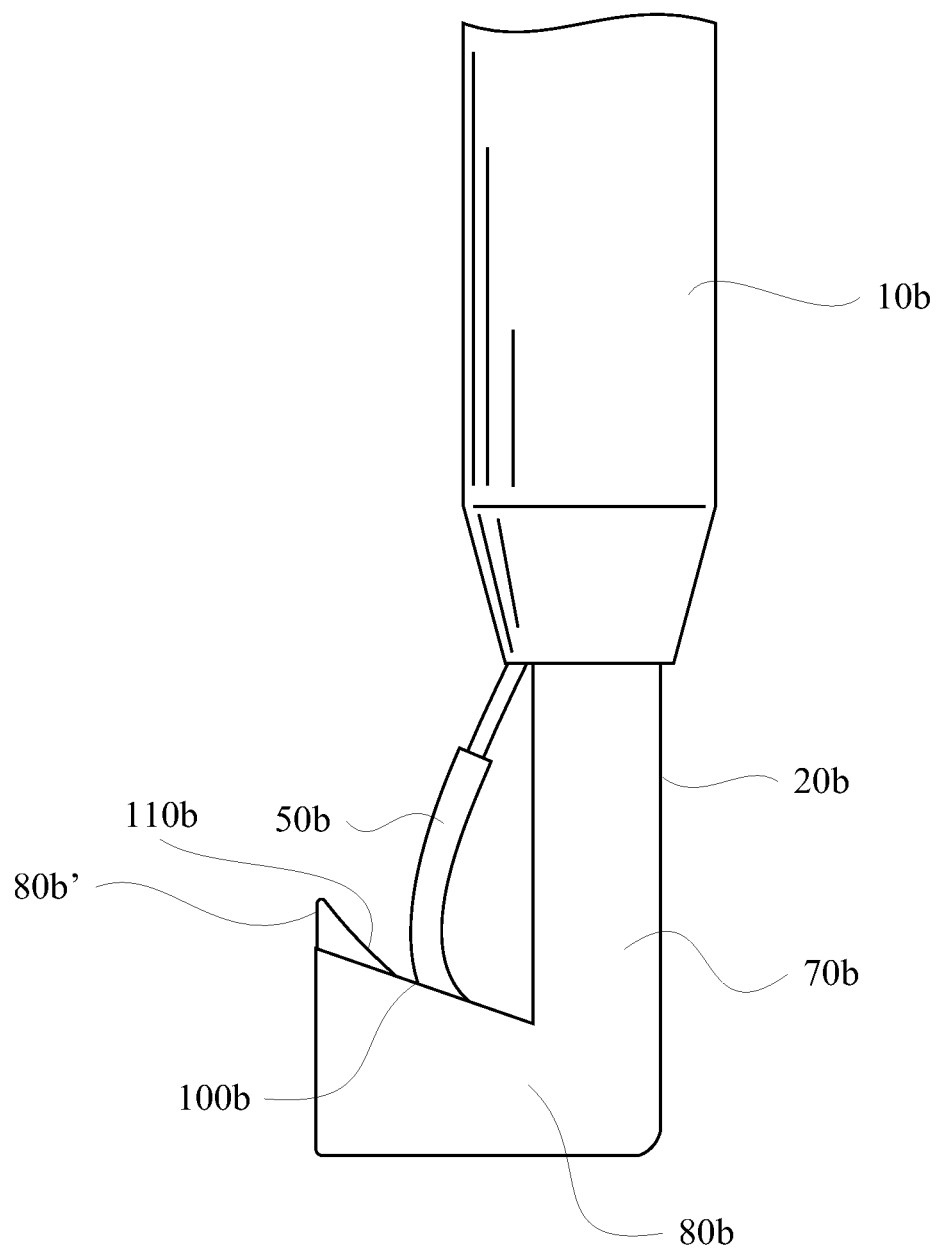
FIG. 12 shows a side view of a downward ramp surgical instrument guide generally positioned perpendicular to the surgical instrument.
Figure 13:
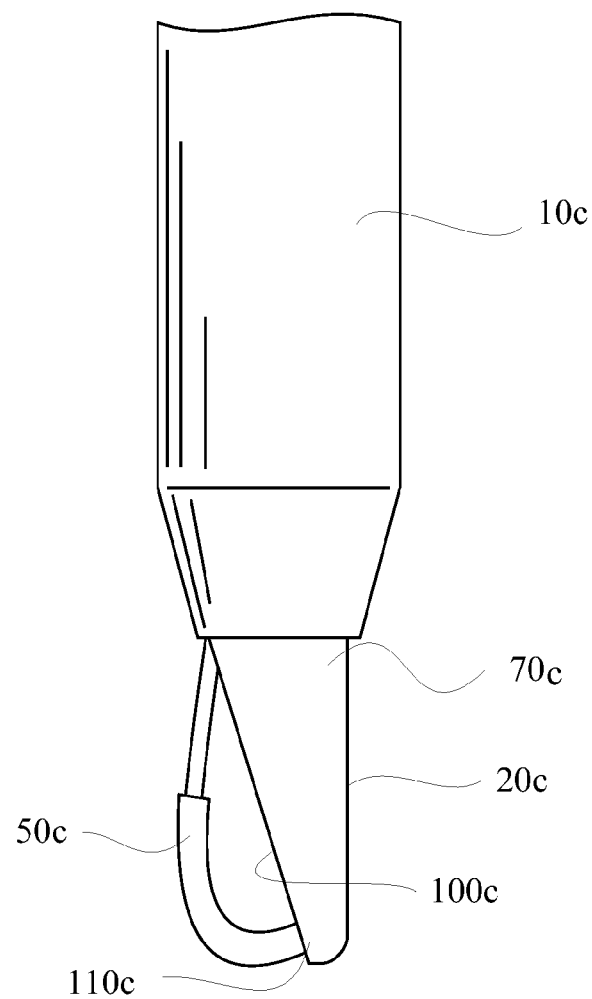
FIG. 13 shows an inline ramp surgical instrument guide.

Turning now to FIGS. 11 to 13, variations of the tissue shield 80 of the guide 20 are discussed. More specifically, the tissue shield 80 and wedge 110 may be altered according to the surgical need. Thus, the angle at which the tissue shield 80 is disposed relative to a surgical instrument 10 may vary and the wedge 110 may be altered to match the desired use and/or positioning of the surgical instrument guide 20.

In FIG. 11, a side view of an alternate configuration of a surgical instrument guide 20a is shown. As shown, the surgical instrument 10a may be held at about a right angle relative to the target tissue to be cut. The guide 20a includes a tissue shield 80a which may extend at about a 90 degree angle relative to the surgical instrument 10a and/or arm 70a for spacing the tissue shield from the surgical instrument. The incline or wedge 110a may have an upper surface 100a with an upward slope. The upward slope causes the target tissue to be lifted along the upper surface 110a of the tissue shield 80a where it contacts the active element 50. The active element 50 may extend into the tissue shield 80a, rather than extending into a depression therein.

Turning now to FIG. 12, a side view of surgical instrument 10b and surgical instrument guide 20b. Rather than an upward incline similar to 110 and 110a in the figures discussed above, the guide 20b includes a downward incline along the tissue shield 80b when the surgical instrument 10b is held vertically. The downward incline 110b allows the tissue shield 80b to function as a hook. The leading edge 80b' can be placed under a target tissue to be cut and the surgical instrument 10b drawn through the target tissue. The hook-like tissue shield 80b lifts the tissue to be cut into contact with the active element 50b, to thereby assist in cutting the target tissue. It also helps prevent tissue(s), other than the target tissue, from contacting the active element 50b.

Turning now to FIG. 13, an inline ramp surgical instrument guide 20c is shown. As can be seen, the guide 20c may allow the surgical tool 10c to be held behind the desired direction of cutting, with the action of pushing the active element 50c along the desired direction of the cut. The wedge or incline 110c at the front of the tissue shield 80c is placed underneath the target tissue and pushed along the direction of the cut. The tissue shield 80c may extend substantially parallel or in-line with the surgical instrument 10c and/or from an arm 70c. The wedge 110c may have a surface 100c having an upward slope toward the active element 50c. The upward slope causes the tissue to be lifted along the top surface 100c of the tissue shield 80c to the active element 50c.

There is thus disclosed a surgical instrument guide. The guide assists a surgeon in cutting through a first layer of tissue, a membrane, etc., while protecting tissue or other physiological structures below or adjacent the target material from being cut. Thus, it will be understood that the term tissue shield may also refer to protecting structures other than tissue. It will be appreciated that numerous changes may be made to the present invention without departing from the scope of the claims.

What is claimed is:

1. A system for treating tissue comprising:
   a surgical instrument comprising an active element shaped for treating tissue; and
   a guide configured for extending from the surgical instrument, the guide including a tissue shield having an inclined surface disposed thereon;
   wherein the tissue shield is disposed adjacent the active element and the inclined surface lifts target tissue into contact with the active element while separating the target tissue from one or more adjacent physiologic structures;
   wherein the tissue shield substantially prevents contact of the active element with the one or more adjacent physiologic structures.

2. The system for treating tissue of claim 1, wherein the tissue shield has a depression formed therein and wherein the active element extends into the depression.

3. The system for treating tissue of claim 1, wherein the tissue shield comprises a planar surface, and wherein the active elements intersects the planar surface.

4. The system for treating tissue of claim 1, wherein the active element extends into the tissue shield.

5. The system for treating tissue of claim 1, wherein the guide comprises a coupling member and wherein the guide is slidably attached to the surgical instrument using the coupling member.

6. The system for treating tissue of claim 1, wherein the guide comprises a coupling member and wherein the coupling member forms a snap-fit connection with the surgical instrument.

7. The system for treating tissue of claim 1, wherein the guide is integrally formed with the surgical instrument.

8. The system for treating tissue of claim 1, wherein the guide is removably attachable to the surgical instrument.

9. The system for treating tissue of claim 1, wherein the active element is a ferromagnetic coated conductor.

10. A guide comprising:
 a coupling member;
 an arm having a first end and a second end, wherein the first end of the arm is attached to the coupling member and the second end of the arm extends away from the coupling member; and
 a shield attached to the second end of the arm.

11. The guide of claim 10, wherein the shield has a top surface having a channel formed therein.

12. The guide of claim 10, further comprising a wedge disposed on the shield for engaging and lifting a material.

13. The guide of claim 10, wherein the arm includes a beveled edge.

14. The guide of claim 10, wherein the shield is disposed substantially perpendicular with the arm.

15. The guide of claim 10, wherein the shield is disposed substantially parallel with the arm.

16. The guide of claim 10, wherein the coupling member is a collar.

17. A method of cutting tissue, the method comprising:
 selecting a surgical instrument having an active element;
 attaching a guide to the surgical instrument such that the guide extends from the surgical instrument adjacent the active element, the guide having a tissue shield with a cutting surface;
 engaging a target tissue with the tissue shield;
 advancing the guide so that tissue slides along the cutting surface of the tissue shield and into contact with the active element to cut the target tissue and substantially prevent the active element from damaging physiologic structures adjacent the target tissue.

18. The method of claim 17, wherein the tissue shield includes an inclined surface for engaging the target tissue, and the method further comprises the step of positioning the inclined surface of the tissue shield between the target tissue and a second tissue and moving the guide such that the inclined surface of the tissue shield separates the target tissue from the second tissue prior to the active element cutting the target tissue.

19. The method of claim 17, wherein the cutting surface of the tissue shield comprises a depression and wherein the guide is attached to the surgical instrument so that the active element extends into the depression and below at least a portion of the cutting surface of the tissue shield.

20. The method of claim 17, wherein the active element is a thermal element, and wherein the method further comprises attaching the guide to the surgical instrument such that transfer of thermal energy from the thermal element to the guide is substantially prevented.

21. The method of claim 17, wherein the active element is a thermally adjustable ferromagnetic coated conductor, and wherein the method further comprises attaching the guide to the surgical instrument such that transfer of thermal energy from the thermally adjustable ferromagnetic coated conductor to the guide is substantially prevented.

* * * * *